(12) United States Patent
Hannula et al.

(10) Patent No.: US 7,698,909 B2
(45) Date of Patent: Apr. 20, 2010

(54) HEADBAND WITH TENSION INDICATOR

(75) Inventors: Don Hannula, San Luis Obispo, CA (US); Joseph Coakley, Dublin, CA (US); Paul D. Mannheimer, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1347 days.

(21) Appl. No.: 10/779,331

(22) Filed: Feb. 13, 2004

(65) Prior Publication Data

US 2004/0221370 A1    Nov. 11, 2004

(51) Int. Cl.
  *D04B 1/24* (2006.01)
(52) U.S. Cl. .......................................... 66/172 E; 2/181
(58) Field of Classification Search ................ 66/169 R, 66/172 E, 170, 171; 2/171, 181, 181.2
See application file for complete search history.

(56) References Cited

U.S. PATENT DOCUMENTS

| | | | |
|---|---|---|---|
| 4,025,733 A | | 5/1977 | Klar et al. |
| 4,047,400 A | * | 9/1977 | Thorneburg .................. 66/171 |
| 4,462,116 A | | 7/1984 | Sanzone et al. |
| 4,499,741 A | * | 2/1985 | Harris .......................... 66/171 |
| 4,510,938 A | | 4/1985 | Jobsis et al. |
| 4,570,638 A | | 2/1986 | Stoddart et al. |
| 4,675,919 A | | 6/1987 | Heine et al. |
| 4,739,757 A | | 4/1988 | Edwards |
| 4,775,116 A | | 10/1988 | Klein |
| 4,784,162 A | | 11/1988 | Ricks et al. |
| 4,802,485 A | | 2/1989 | Bowers et al. |
| 4,825,872 A | | 5/1989 | Tan et al. |
| 4,825,879 A | | 5/1989 | Tan et al. |

(Continued)

FOREIGN PATENT DOCUMENTS

CN        1306260        8/2001

(Continued)

OTHER PUBLICATIONS

U.S. Appl. No. 10/677,742, filed Oct. 1, 2003, Hannula et al.

(Continued)

*Primary Examiner*—Danny Worrell
(74) *Attorney, Agent, or Firm*—Fletcher Yoder

(57) ABSTRACT

A headband having a low stretch segment sized to fit around a wearer's head, and an elastic segment being smaller than the low stretch segment, and having a free end and an attached end, where the elastic segment is attached at its attached end with the low stretch segment. The headband also includes a tab portion having a first end and a second end, the first end of the tab portion being connected with the free end of the elastic portion, the second end of the tab portion configured to form a closed loop with the low stretch segment, around the wearer's head. The headband also includes visual indicator configured for monitoring the extended position of elastic segment and optionally a stop portion that is configured to engage against the elastic segment to limit its stretch. When having a stop portion, the tab portion also includes an indicator portion between its first end and the stop portion such that the indicator portion when visible indicates that the headband needs re-tightening; and when the indicator portion is not visible it indicates an adequate level of tension corresponding with delivering a pressure in the range higher than the venous pressure and lower than the capillary pressure to the forehead of the wearer.

18 Claims, 6 Drawing Sheets

U.S. PATENT DOCUMENTS

| | | | |
|---|---|---|---|
| 4,833,734 A * | 5/1989 | Der Estephanian | 2/171 |
| 4,838,279 A | 6/1989 | Fore | |
| 4,856,116 A | 8/1989 | Sullivan | |
| 4,890,619 A | 1/1990 | Hatschek | |
| 4,910,804 A * | 3/1990 | Lidgren | 2/209.3 |
| 4,918,758 A * | 4/1990 | Rendina | 2/171 |
| 4,930,888 A | 6/1990 | Freisleben et al. | |
| 4,942,877 A | 7/1990 | Sakai et al. | |
| 4,972,331 A | 11/1990 | Chance | |
| 4,977,011 A | 12/1990 | Smith | |
| 4,991,234 A | 2/1991 | Greenberg | |
| 4,996,975 A | 3/1991 | Nakamura | |
| 5,005,374 A | 4/1991 | Spitler et al. | |
| 5,054,488 A | 10/1991 | Muz | |
| 5,080,096 A | 1/1992 | Hooper et al. | |
| 5,080,098 A | 1/1992 | Willett et al. | |
| H1039 H | 4/1992 | Tripp, Jr. et al. | |
| 5,111,817 A | 5/1992 | Clark et al. | |
| 5,119,815 A | 6/1992 | Chance | |
| 5,122,974 A | 6/1992 | Chance | |
| 5,125,403 A | 6/1992 | Culp | |
| 5,167,230 A | 12/1992 | Chance | |
| 5,188,108 A | 2/1993 | Secker | |
| 5,191,891 A | 3/1993 | Righter | |
| 5,209,230 A | 5/1993 | Swedlow et al. | |
| 5,214,409 A | 5/1993 | Beigel | |
| 5,217,012 A | 6/1993 | Young et al. | |
| 5,217,013 A | 6/1993 | Lewis et al. | |
| 5,241,300 A | 8/1993 | Buschmann | |
| 5,246,003 A | 9/1993 | DeLonzor | |
| 5,253,645 A | 10/1993 | Friedman et al. | |
| 5,267,563 A | 12/1993 | Swedlow et al. | |
| 5,267,567 A | 12/1993 | Aung et al. | |
| 5,295,490 A | 3/1994 | Dodakian | |
| 5,313,940 A | 5/1994 | Fuse et al. | |
| 5,337,744 A | 8/1994 | Branigan | |
| 5,348,008 A | 9/1994 | Bornn et al. | |
| 5,353,798 A | 10/1994 | Sieben | |
| 5,354,979 A | 10/1994 | Adelson et al. | |
| 5,357,953 A | 10/1994 | Merrick et al. | |
| 5,368,025 A | 11/1994 | Young et al. | |
| 5,368,562 A | 11/1994 | Blomquist et al. | |
| 5,383,874 A | 1/1995 | Jackson et al. | |
| 5,392,777 A | 2/1995 | Swedlow et al. | |
| 5,398,689 A | 3/1995 | Conner et al. | |
| 5,400,267 A | 3/1995 | Denen et al. | |
| 5,405,269 A | 4/1995 | Stupecky | |
| 5,405,614 A | 4/1995 | D'Angelo et al. | |
| 5,413,099 A | 5/1995 | Schmidt et al. | |
| 5,413,101 A | 5/1995 | Sugiura | |
| 5,413,102 A | 5/1995 | Schmidt et al. | |
| 5,415,166 A | 5/1995 | Imran | |
| 5,425,360 A | 6/1995 | Nelson | |
| 5,431,170 A | 7/1995 | Mathews | |
| 5,437,275 A | 8/1995 | Amundsen et al. | |
| 5,437,634 A | 8/1995 | Amano | |
| 5,444,254 A | 8/1995 | Thomson | |
| 5,451,763 A | 9/1995 | Pickett et al. | |
| 5,452,717 A | 9/1995 | Branigan et al. | |
| 5,465,714 A | 11/1995 | Scheuing | |
| 5,469,845 A | 11/1995 | DeLonzor et al. | |
| 5,482,034 A | 1/1996 | Lewis | |
| 5,490,523 A | 2/1996 | Isaacson | |
| 5,528,519 A | 6/1996 | Ohkura et al. | |
| 5,546,955 A | 8/1996 | Wilk | |
| 5,551,423 A | 9/1996 | Sugiura | |
| 5,562,718 A | 10/1996 | Palermo | |
| 5,564,108 A | 10/1996 | Hunsaker et al. | |
| 5,564,417 A | 10/1996 | Chance | |
| 5,584,296 A | 12/1996 | Cui et al. | |
| 5,592,408 A | 1/1997 | Keskin et al. | |
| 5,596,987 A | 1/1997 | Chance | |
| 5,617,865 A | 4/1997 | Palczewska et al. | |
| 5,617,866 A | 4/1997 | Marian, Jr. | |
| 5,627,323 A | 5/1997 | Stern | |
| 5,634,466 A | 6/1997 | Gruner | |
| 5,638,593 A | 6/1997 | Gerhardt et al. | |
| 5,638,818 A | 6/1997 | Diab et al. | |
| 5,640,953 A | 6/1997 | Bishop et al. | |
| 5,645,440 A | 7/1997 | Tobler et al. | |
| 5,645,586 A | 7/1997 | Meltzer | |
| 5,646,416 A | 7/1997 | Van De Velde | |
| 5,671,750 A | 9/1997 | Shinoda | |
| 5,673,708 A | 10/1997 | Athanasiou et al. | |
| 5,678,544 A | 10/1997 | DeLonzor et al. | |
| 5,681,285 A | 10/1997 | Ford et al. | |
| 5,683,434 A | 11/1997 | Archer | |
| 5,697,363 A | 12/1997 | Hart | |
| 5,697,367 A | 12/1997 | Lewis et al. | |
| 5,701,894 A | 12/1997 | Cherry et al. | |
| 5,706,820 A | 1/1998 | Hossack et al. | |
| 5,732,475 A | 3/1998 | Sacks et al. | |
| 5,738,612 A | 4/1998 | Tsuda | |
| 5,743,856 A | 4/1998 | Oka et al. | |
| 5,743,857 A | 4/1998 | Shinoda et al. | |
| 5,752,913 A | 5/1998 | Oka | |
| 5,752,920 A | 5/1998 | Ogura et al. | |
| 5,758,644 A | 6/1998 | Diab et al. | |
| 5,772,601 A | 6/1998 | Oka et al. | |
| 5,776,058 A | 7/1998 | Levinson et al. | |
| 5,776,071 A | 7/1998 | Inuaki et al. | |
| 5,779,631 A | 7/1998 | Chance | |
| 5,779,639 A | 7/1998 | Yeung | |
| 5,782,757 A | 7/1998 | Diab et al. | |
| 5,786,592 A | 7/1998 | Hök | |
| 5,791,347 A | 8/1998 | Flaherty et al. | |
| 5,791,348 A | 8/1998 | Aung et al. | |
| 5,792,052 A | 8/1998 | Isaacson | |
| 5,792,058 A | 8/1998 | Lee et al. | |
| 5,797,841 A | 8/1998 | Delonzor et al. | |
| 5,810,724 A | 9/1998 | Gronvall | |
| 5,813,980 A | 9/1998 | Levinson et al. | |
| 5,823,012 A * | 10/1998 | Hacskaylo | 66/171 |
| 5,823,952 A | 10/1998 | Levinson et al. | |
| 5,826,277 A | 10/1998 | McConville | |
| 5,830,136 A | 11/1998 | Delonzor et al. | |
| 5,830,137 A | 11/1998 | Scharf | |
| 5,830,148 A | 11/1998 | Inuaki et al. | |
| 5,830,149 A | 11/1998 | Oka et al. | |
| 5,833,602 A | 11/1998 | Osemwota | |
| 5,836,887 A | 11/1998 | Oka et al. | |
| 5,839,439 A | 11/1998 | Nierlich et al. | |
| RE36,000 E | 12/1998 | Swedlow et al. | |
| 5,842,981 A | 12/1998 | Larsen et al. | |
| 5,842,982 A | 12/1998 | Mannheimer | |
| 5,851,179 A | 12/1998 | Ritson et al. | |
| 5,857,974 A | 1/1999 | Eberle et al. | |
| 5,860,932 A | 1/1999 | Goto et al. | |
| 5,860,957 A | 1/1999 | Jacobsen et al. | |
| 5,868,133 A | 2/1999 | DeVries et al. | |
| 5,870,626 A | 2/1999 | Lebeau | |
| 5,872,713 A | 2/1999 | Douglas et al. | |
| 5,873,821 A | 2/1999 | Chance et al. | |
| 5,879,294 A | 3/1999 | Anderson et al. | |
| 5,891,021 A | 4/1999 | Dillon et al. | |
| 5,891,026 A | 4/1999 | Wang et al. | |
| 5,895,359 A | 4/1999 | Peel | |
| 5,902,235 A | 5/1999 | Lewis et al. | |
| 5,906,581 A | 5/1999 | Tsuda | |
| 5,913,819 A | 6/1999 | Taylor et al. | |
| 5,916,154 A | 6/1999 | Hobbs et al. | |
| 5,919,133 A | 7/1999 | Taylor et al. | |
| 5,931,790 A | 8/1999 | Peel | |
| 5,931,791 A | 8/1999 | Saltzstein et al. | |

| | | | | | | |
|---|---|---|---|---|---|---|
| 5,934,925 | A | 8/1999 | Tobler et al. | 6,321,100 B1 | 11/2001 | Parker |
| 5,936,539 | A | 8/1999 | Fuchs | 6,322,516 B1 | 11/2001 | Masuda et al. |
| 5,947,905 | A | 9/1999 | Hadjicostis et al. | 6,343,223 B1 | 1/2002 | Chin et al. |
| 5,954,053 | A | 9/1999 | Chance et al. | 6,343,224 B1 | 1/2002 | Parker |
| 5,957,850 | A | 9/1999 | Marian, Jr. et al. | 6,346,886 B1 | 2/2002 | De La Huerga |
| 5,964,701 | A | 10/1999 | Asada et al. | 6,349,228 B1 | 2/2002 | Kiani et al. |
| 5,980,464 | A | 11/1999 | Tsuda | 6,356,774 B1 | 3/2002 | Bernstein et al. |
| 5,983,129 | A | 11/1999 | Cowan et al. | 6,362,622 B1 | 3/2002 | Stauber et al. |
| 5,987,343 | A | 11/1999 | Kinast | 6,368,282 B1 | 4/2002 | Oka et al. |
| 5,987,351 | A | 11/1999 | Chance | 6,370,411 B1 | 4/2002 | Osadchy et al. |
| 5,991,648 | A | 11/1999 | Levin | 6,377,829 B1 | 4/2002 | Al-Ali |
| 5,995,077 | A | 11/1999 | Wilcox et al. | 6,381,480 B1 | 4/2002 | Stoddart et al. |
| 5,995,855 | A | 11/1999 | Kiani et al. | 6,381,481 B1 | 4/2002 | Levendowski et al. |
| 5,995,856 | A | 11/1999 | Mannheimer et al. | 6,385,486 B1 | 5/2002 | John et al. |
| 5,995,857 | A | 11/1999 | Toomim et al. | 6,385,821 B1 | 5/2002 | Modgil et al. |
| 6,007,492 | A | 12/1999 | Goto et al. | 6,387,092 B1 | 5/2002 | Burnside et al. |
| 6,011,986 | A | 1/2000 | Diab et al. | 6,388,240 B2 | 5/2002 | Schulz et al. |
| 6,022,320 | A | 2/2000 | Ogura et al. | 6,397,091 B2 | 5/2002 | Diab et al. |
| 6,027,453 | A | 2/2000 | Miwa et al. | 6,405,075 B1 | 6/2002 | Levin |
| 6,030,351 | A | 2/2000 | Schmidt et al. | 6,416,471 B1 | 7/2002 | Kumar et al. |
| 6,031,603 | A | 2/2000 | Fine et al. | 6,416,474 B1 | 7/2002 | Penner et al. |
| 6,036,651 | A | 3/2000 | Inuaki et al. | 6,417,774 B1 | 7/2002 | Hibbs et al. |
| 6,041,247 | A | 3/2000 | Weckstrom et al. | 6,423,010 B1 | 7/2002 | Friedman et al. |
| 6,047,201 | A | 4/2000 | Jackson | 6,430,423 B2 | 8/2002 | DeLonzor et al. |
| 6,047,203 | A | 4/2000 | Sackner et al. | 6,432,050 B1 | 8/2002 | Porat et al. |
| 6,049,958 | A | 4/2000 | Eberle et al. | 6,450,168 B1 | 9/2002 | Nguyen |
| 6,050,951 | A | 4/2000 | Friedman et al. | 6,450,957 B1 | 9/2002 | Yoshimi et al. |
| 6,052,619 | A | 4/2000 | John | 6,450,981 B1 | 9/2002 | Shabty et al. |
| 6,073,038 | A | 6/2000 | Wang et al. | 6,454,708 B1 | 9/2002 | Ferguson et al. |
| 6,084,380 | A | 7/2000 | Burton | 6,461,305 B1 | 10/2002 | Schnall |
| 6,085,752 | A | 7/2000 | Kehr et al. | 6,463,310 B1 | 10/2002 | Swedlow et al. |
| 6,088,607 | A | 7/2000 | Diab et al. | 6,466,809 B1 | 10/2002 | Riley |
| 6,106,780 | A | 8/2000 | Douglas et al. | 6,468,241 B1 | 10/2002 | Gelfand et al. |
| 6,112,107 | A | 8/2000 | Hannula | 6,470,199 B1 | 10/2002 | Kopotic et al. |
| 6,115,621 | A | 9/2000 | Chin | 6,470,279 B1 | 10/2002 | Samsoondar |
| 6,118,382 | A | 9/2000 | Hibbs et al. | 6,480,762 B1 | 11/2002 | Uchikubo et al. |
| 6,134,459 | A | 10/2000 | Roberts et al. | 6,491,638 B2 | 12/2002 | Oka |
| 6,144,868 | A | 11/2000 | Parker | 6,491,639 B1 | 12/2002 | Turcott |
| 6,149,481 | A | 11/2000 | Wang et al. | 6,503,087 B1 | 1/2003 | Eggert et al. |
| 6,152,754 | A | 11/2000 | Gerhardt et al. | 6,503,204 B1 | 1/2003 | Sumaneweera et al. |
| 6,154,667 | A | 11/2000 | Miura et al. | 6,505,061 B2 | 1/2003 | Larson |
| 6,162,188 | A | 12/2000 | Barnea | 6,511,478 B1 | 1/2003 | Burnside et al. |
| 6,165,173 | A | 12/2000 | Kamdar et al. | 6,516,289 B2 | 2/2003 | David |
| 6,171,258 | B1 | 1/2001 | Karakasoglu et al. | 6,519,487 B1 | 2/2003 | Parker |
| 6,173,196 | B1 | 1/2001 | Delonzor et al. | 6,524,257 B2 | 2/2003 | Ogura |
| 6,179,786 | B1 | 1/2001 | Young | 6,525,386 B1 | 2/2003 | Mills et al. |
| 6,181,959 | B1 | 1/2001 | Schollermann et al. | 6,526,309 B1 | 2/2003 | Chance |
| 6,184,521 | B1 | 2/2001 | Coffin, IV et al. | 6,526,970 B2 | 3/2003 | DeVries et al. |
| 6,186,953 | B1 | 2/2001 | Narimatsu | 6,527,725 B1 | 3/2003 | Inuaki et al. |
| 6,186,954 | B1 | 2/2001 | Narimatsu | 6,527,726 B2 | 3/2003 | Goto et al. |
| 6,190,325 | B1 | 2/2001 | Narimatsu | 6,535,765 B1 | 3/2003 | Amely-Velez et al. |
| 6,196,974 | B1 | 3/2001 | Miwa | 6,537,220 B1 | 3/2003 | Friemel et al. |
| 6,198,952 | B1 | 3/2001 | Miesel | 6,541,756 B2 | 4/2003 | Schulz et al. |
| 6,199,550 | B1 | 3/2001 | Wiesmann et al. | 6,542,081 B2 | 4/2003 | Torch |
| 6,209,144 | B1 | 4/2001 | Carter | 6,547,742 B2 | 4/2003 | Oka et al. |
| 6,216,021 | B1 | 4/2001 | Franceschini et al. | 6,547,743 B2 | 4/2003 | Brydon |
| 6,223,063 | B1 | 4/2001 | Chaiken et al. | 6,551,252 B2 | 4/2003 | Sackner et al. |
| 6,241,680 | B1 | 6/2001 | Miwa | 6,553,242 B1 | 4/2003 | Sarussi |
| 6,248,083 | B1 | 6/2001 | Smith et al. | 6,575,902 B1 | 6/2003 | Burton |
| 6,251,076 | B1 | 6/2001 | Hovland et al. | 6,575,904 B2 | 6/2003 | Nagai et al. |
| 6,251,080 | B1 | 6/2001 | Henkin et al. | 6,580,086 B1 | 6/2003 | Schulz et al. |
| 6,251,081 | B1 | 6/2001 | Narimatsu | 6,582,371 B2 | 6/2003 | Miller |
| 6,251,113 | B1 | 6/2001 | Appelbaum et al. | 6,582,374 B2 | 6/2003 | Yokozeki |
| 6,256,523 | B1 | 7/2001 | Diab et al. | 6,584,356 B2 | 6/2003 | Wassmund et al. |
| 6,256,524 | B1 | 7/2001 | Walker et al. | 6,589,171 B2 | 7/2003 | Keirsbilck |
| 6,263,221 | B1 | 7/2001 | Chance et al. | 6,589,183 B2 | 7/2003 | Yokozeki |
| 6,263,223 | B1 | 7/2001 | Shepherd et al. | 6,589,189 B2 | 7/2003 | Meyerson et al. |
| 6,280,213 | B1 | 8/2001 | Tobler et al. | 6,594,513 B1 | 7/2003 | Jobsis et al. |
| 6,282,450 | B1 | 8/2001 | Hartlaub et al. | 6,597,933 B2 | 7/2003 | Kiani et al. |
| 6,283,922 | B1 | 9/2001 | Goto et al. | 6,605,038 B1 | 8/2003 | Teller et al. |
| 6,285,895 | B1 | 9/2001 | Ristolainen et al. | 6,606,993 B1 | 8/2003 | Wiesmann et al. |
| 6,306,076 | B1 | 10/2001 | Gill | 6,611,793 B1 | 8/2003 | Burnside et al. |
| 6,308,089 | B1 | 10/2001 | von der Ruhr et al. | 6,615,065 B1 | 9/2003 | Barrett et al. |

| | | | | | | |
|---|---|---|---|---|---|---|
| 6,622,034 | B1 | 9/2003 | Gorski et al. | 2003/0120183 A1 | 6/2003 | Simmons |
| 6,635,048 | B1 | 10/2003 | Ullestad et al. | 2003/0122706 A1 | 7/2003 | Choi et al. |
| 6,640,116 | B2 | 10/2003 | Diab | 2003/0125616 A1 | 7/2003 | Black et al. |
| 6,645,154 | B2 | 11/2003 | Oka | 2003/0135127 A1 | 7/2003 | Sackner et al. |
| 6,645,155 | B2 | 11/2003 | Inuaki et al. | 2003/0144579 A1 | 7/2003 | Buss |
| 6,653,557 | B2 | 11/2003 | Wolf et al. | 2003/0156288 A1 | 8/2003 | Barnum et al. |
| 6,654,622 | B1 | 11/2003 | Eberhard et al. | 2003/0176810 A1 | 9/2003 | Maahs et al. |
| 6,662,033 | B2 | 12/2003 | Casciani et al. | 2003/0189492 A1 | 10/2003 | Harvie |
| 6,666,860 | B2 | 12/2003 | Takahashi | 2003/0216728 A1 | 11/2003 | Stern et al. |
| 6,671,531 | B2 | 12/2003 | Al-Ali et al. | 2003/0225323 A1 | 12/2003 | Kiani et al. |
| 6,671,545 | B2 | 12/2003 | Fincke | 2004/0002655 A1 | 1/2004 | Bolorforosh et al. |
| 6,678,543 | B2 | 1/2004 | Diab et al. | 2004/0007585 A1 | 1/2004 | Griffith et al. |
| 6,681,454 | B2 | 1/2004 | Modgil et al. | 2004/0030258 A1 | 2/2004 | Williams et al. |
| 6,684,091 | B2 | 1/2004 | Parker | 2004/0044545 A1 | 3/2004 | Wiesmann et al. |
| 6,704,601 | B1 | 3/2004 | Amely-Velez et al. | 2004/0117891 A1 | 6/2004 | Hannula et al. |
| 6,736,759 | B1 | 5/2004 | Stubbs et al. | 2004/0163648 A1 | 8/2004 | Burton |
| 6,748,254 | B2 | 6/2004 | O'Neil et al. | 2005/0027207 A1 | 2/2005 | Westbrook et al. |
| 6,811,538 | B2 | 11/2004 | Westbrook et al. | 2005/0059869 A1 | 3/2005 | Scharf et al. |
| 6,934,570 | B2 | 8/2005 | Kiani et al. | 2005/0070776 A1 | 3/2005 | Mannheimer et al. |
| 6,934,571 | B2 | 8/2005 | Wiesmann et al. | 2005/0113656 A1 | 5/2005 | Chance |
| 6,985,763 | B2 | 1/2006 | Boas et al. | 2005/0188991 A1 | 9/2005 | Sun et al. |
| 7,001,334 | B2 | 2/2006 | Reed et al. | 2005/0261594 A1 | 11/2005 | Banet |
| 7,027,850 | B2 | 4/2006 | Wasserman | 2005/0277819 A1 | 12/2005 | Kiani et al. |
| 7,047,054 | B2 | 5/2006 | Benni | 2006/0195026 A1 | 8/2006 | Casciani et al. |
| 7,047,055 | B2 | 5/2006 | Boas et al. | 2006/0195027 A1 | 8/2006 | Casciani et al. |
| 7,054,453 | B2 | 5/2006 | Causevic et al. | 2006/0211929 A1 | 9/2006 | Casciani et al. |
| 7,054,454 | B2 | 5/2006 | Causevic et al. | 2006/0217604 A1 | 9/2006 | Fein et al. |
| 7,072,704 | B2 | 7/2006 | Bucholz | 2006/0217605 A1 | 9/2006 | Fein et al. |
| 7,085,597 | B2 | 8/2006 | Fein et al. | 2006/0217606 A1 | 9/2006 | Fein et al. |
| 7,113,815 | B2 | 9/2006 | O'Neil et al. | 2006/0217607 A1 | 9/2006 | Fein et al. |
| 7,132,641 | B2 | 11/2006 | Schulz et al. | 2006/0217608 A1 | 9/2006 | Fein et al. |
| 7,171,251 | B2 | 1/2007 | Sarussi et al. | 2006/0229510 A1 | 10/2006 | Fein et al. |
| 7,181,264 | B2 | 2/2007 | Wiesmann et al. | 2006/0229511 A1 | 10/2006 | Fein et al. |
| 7,190,999 | B2 | 3/2007 | Geheb et al. | 2006/0264726 A1 | 11/2006 | Mannheimer et al. |
| 7,204,250 | B1 | 4/2007 | Burton | 2006/0264727 A1 | 11/2006 | Mannheimer et al. |
| 7,220,220 | B2 | 5/2007 | Stubbs et al. | 2006/0276700 A1 | 12/2006 | O'Neil et al. |
| 7,231,240 | B2 | 6/2007 | Eda et al. | 2006/0281984 A1 | 12/2006 | Mannheimer et al. |
| 7,245,953 | B1 | 7/2007 | Parker | 2007/0032732 A1 | 2/2007 | Shelley et al. |
| 7,248,910 | B2 | 7/2007 | Li et al. | 2007/0149871 A1 | 6/2007 | Sarussi et al. |
| 7,289,837 | B2 | 10/2007 | Mannheimer et al. | 2007/0293746 A1 | 12/2007 | Sarussi et al. |
| 7,297,119 | B2 | 11/2007 | Westbrook et al. | 2008/0009691 A1 | 1/2008 | Parker |
| 7,305,262 | B2 | 12/2007 | Brodnick et al. | 2008/0045822 A1 | 2/2008 | Phillips et al. |
| 7,313,427 | B2 | 12/2007 | Benni | 2008/0076988 A1 | 3/2008 | Sarussi et al. |
| 7,349,726 | B2 | 3/2008 | Casciani et al. | 2008/0076990 A1 | 3/2008 | Sarussi et al. |
| 7,367,949 | B2 | 5/2008 | Korhonen et al. | | | |
| 7,376,454 | B2 | 5/2008 | Casciani et al. | | | |
| 7,415,298 | B2 | 8/2008 | Casciani et al. | | | |

FOREIGN PATENT DOCUMENTS

| | | |
|---|---|---|
| DE | 3705493 | 8/1988 |
| DE | 3744781 | 1/1989 |
| DE | 3810411 | 10/1989 |
| DE | 3927038 | 2/1991 |
| DE | 4429845 | 10/1995 |
| DE | 29515877 U1 | 11/1995 |
| DE | 19541605 | 5/1997 |
| DE | 19939302 | 5/2001 |
| DE | 10029205 | 1/2002 |
| EP | 268850 | 6/1988 |
| EP | 0313238 | 4/1989 |
| EP | 338518 | 10/1989 |
| EP | 463620 | 1/1992 |
| EP | 543172 | 5/1993 |
| EP | 0572684 | 12/1993 |
| EP | 0573137 | 12/1993 |
| EP | 578530 | 1/1994 |
| EP | 580385 | 1/1994 |
| EP | 775311 | 8/1994 |
| EP | 621026 | 10/1994 |
| EP | 0631756 | 1/1995 |
| EP | 0631756 A1 | 1/1995 |
| EP | 665025 | 8/1995 |
| EP | 0695139 | 2/1996 |
| EP | 0721110 | 7/1996 |
| EP | 1048323 | 2/2000 |

2001/0000790 A1 5/2001 DeLonzor et al.
2001/0009398 A1 7/2001 Sekura et al.
2002/0013538 A1 1/2002 Teller
2002/0042558 A1 4/2002 Mendelson
2002/0052539 A1 5/2002 Haller et al.
2002/0084904 A1 7/2002 De La Huerga
2002/0091335 A1 7/2002 John et al.
2002/0095092 A1 7/2002 Kondo et al.
2002/0103445 A1 8/2002 Rahdert et al.
2002/0109600 A1 8/2002 Mault et al.
2002/0124295 A1 9/2002 Fenwick et al.
2002/0139368 A1 10/2002 Bashinski
2002/0148470 A1 10/2002 Blue et al.
2002/0151929 A1 10/2002 Goto et al.
2002/0156354 A1 10/2002 Larson
2002/0161309 A1 10/2002 Marro
2002/0173706 A1 11/2002 Takatani et al.
2002/0173708 A1 11/2002 DeLonzor et al.
2003/0004547 A1 1/2003 Owens et al.
2003/0009119 A1 1/2003 Kamm et al.
2003/0009308 A1 1/2003 Kirtley
2003/0018243 A1 1/2003 Gerhardt et al.
2003/0023140 A1 1/2003 Chance
2003/0036685 A1 2/2003 Goodman
2003/0065275 A1 4/2003 Mault et al.
2003/0086156 A1 5/2003 McGuire

| | | | | | | |
|---|---|---|---|---|---|---|
| EP | 996063 | 4/2000 | | WO | WO 9118550 | 12/1991 |
| EP | 1130412 | 5/2001 | | WO | WO 9220273 | 11/1992 |
| EP | 1169965 | 1/2002 | | WO | WO 95/06430 | 3/1995 |
| EP | 1547515 | 6/2005 | | WO | WO9512349 | 5/1995 |
| FR | 2555744 | 11/1983 | | WO | WO 9615714 | 5/1996 |
| FR | 2601137 | 1/1988 | | WO | WO 9616591 | 6/1996 |
| GB | 2135074 | 8/1984 | | WO | WO 9641138 | 12/1996 |
| GB | 834 469 | 5/1992 | | WO | WO 9720494 | 6/1997 |
| GB | 2390903 | 1/2004 | | WO | WO 9720497 | 6/1997 |
| JP | 55024614 | 2/1980 | | WO | WO9817174 | 4/1998 |
| JP | 04057161 | 2/1992 | | WO | WO9947039 | 9/1999 |
| JP | 07336597 | 12/1995 | | WO | WO 9963883 | 12/1999 |
| JP | 08111295 | 4/1996 | | WO | WO0059374 | 10/2000 |
| JP | 08112257 | 5/1996 | | WO | WO 00/78209 | 12/2000 |
| JP | 08336546 | 12/1996 | | WO | WO 01/01855 | 1/2001 |
| JP | 09010319 | 1/1997 | | WO | WO 01/17425 | 3/2001 |
| JP | 09154937 | 6/1997 | | WO | WO0176471 | 10/2001 |
| JP | 10314149 | 12/1998 | | WO | WO 01/87224 | 11/2001 |
| JP | 11259583 | 9/1999 | | WO | WO 02/15784 | 2/2002 |
| JP | 2000/189440 | 7/2000 | | WO | WO 02/065901 | 8/2002 |
| JP | 2001/161648 | 6/2001 | | WO | WO 02066977 | 8/2002 |
| JP | 2001/190498 | 7/2001 | | WO | WO 02/089664 | 11/2002 |
| JP | 2001/308576 | 11/2001 | | WO | WO 03/026558 | 4/2003 |
| JP | 2001/332832 | 11/2001 | | WO | WO 03/057030 | 7/2003 |
| JP | 2001/346775 | 12/2001 | | WO | WO03071928 | 9/2003 |
| JP | 2002/065647 | 3/2002 | | WO | WO 03080152 | 10/2003 |
| JP | 2003/210402 | 7/2003 | | WO | WO2005010568 | 2/2005 |
| JP | 2003/235813 | 8/2003 | | | | |
| JP | 2003/265425 | 9/2003 | | | | |
| JP | 2004/016659 | 1/2004 | | | | |
| JP | 2004/065832 | 3/2004 | | | | |
| RU | 2132204 | 6/1999 | | | | |
| WO | WO9001293 | 2/1990 | | | | |
| WO | WO9111137 | 8/1991 | | | | |
| WO | WO 9115151 | 10/1991 | | | | |

OTHER PUBLICATIONS

Letter dated May 13, 2003 to Howard Alhanati (Custom Fab Inc.) from Joe Coakley (TYCO Healthcare Nellcor); 1p.

Nellcor Puritan Bennett "Specification, Headband, Posey, Maxfast" Apr. 4, 2002; 1p.

* cited by examiner

HEADBAND WITH TENSION INDICATOR

BACKGROUND OF THE INVENTION

The present invention relates to headbands, and in particular to headbands that have a tension indicator for indicating when a headband is appropriately stretched and is thus capable of imparting an appropriate level of pressure to a wearer's head.

Various headband devices are known. These include athletic type headband devices as well as more sophisticated headband devices, such as those used to mount devices carried on the head. Some headband devices are used to apply a certain level of pressure to the region under the headband. Such applied pressures are useful, for example, to support a medical sensor for the wearer of the headband. In such circumstances, there is a need for an improved headband having a tension indicator.

BRIEF SUMMARY OF THE INVENTION

Embodiments of the present invention are directed to a headband device. In one embodiment, the present invention provides a headband having a low stretch segment sized to fit around a wearer's head; and an elastic segment being smaller than the low stretch segment. The elastic segment has a free end and an attached end, where the elastic segment is attached at its attached end with the low stretch segment, and the free end of the elastic segment is configured to form a closed loop with the low stretch segment around a wearer's head.

In one aspect, the headband also includes a visual indicator that is configured for monitoring the extended position of the free end of the elastic segment. The visual indicator can be a notch, a line or a marking on the low stretch segment.

In one aspect, the headband also includes a stop portion, where the stop portion is configured to engage against the elastic segment to limit the stretch of the elastic segment. In one embodiment, the stop portion has an opening having a width that is smaller than the width of the low stretch segment and the width of the elastic segment.

In another aspect, the headband also includes a closure mechanism configured to couple the free end of the elastic portion with the low stretch segment to secure the closed loop. The closure mechanism can be a hook and loop closure, a snap, a button, an adhesive, a pin, or combinations thereof.

In another aspect, the headband also includes a tab portion having a first end and a second end, where the first end of the tab portion is connected with the free end of the elastic portion, and the second end of the tab portion is configured to form a closed loop with the low stretch segment.

In one aspect, the tab portion is less elastic than the elastic portion.

In another aspect, the headband also includes a stop portion, where the stop portion is configured to engage against the elastic segment to limit the stretch of the elastic segment. The tab portion also includes an indicator portion between its first end and the stop portion such that the indicator portion when visible indicates that the headband needs re-tightening; and when the indicator portion is not visible it indicates an adequate level of tension corresponding with delivering a pressure in the range higher than the venous pressure and lower than the capillary pressure to the forehead of the wearer.

In another aspect, the present invention provides a headband for applying pressure to an oximetry sensor on the forehead of a patient. The headband includes a low stretch segment sized to fit around a patient's head, and an elastic segment being smaller than the low stretch segment. The elastic segment has a free end and an attached end, where the elastic segment is attached at its attached end with the low stretch segment. The headband also includes a tab portion having a first end and a second end, where the first end of the tab portion is connected with the free end of the elastic portion, and the second end of the tab portion is configured to form a closed loop with the low stretch segment around a patient's head. The headband also includes a visual indicator that is configured to show the extended position for the elastic segment. The headband also includes a stop portion, where the stop portion is configured to engage against the elastic segment to limit the stretch of the elastic segment. The stop portion has an opening having a width that is smaller than the width of the low stretch segment and the width of the elastic segment. The headband also has a closure mechanism configured to couple the second end of the tab portion with the low stretch segment to secure the closed loop.

In one aspect, the tab portion includes an indicator portion between its first end and the stop portion such that the indicator portion when visible indicates that the headband needs re-tightening; and when the indicator portion is not visible it indicates an adequate level of tension corresponding with delivering a pressure in the range higher than the venous pressure and lower than the capillary pressure to the forehead of the patient.

In another aspect, the indicator is a notch, a line or a marking on the low stretch segment.

For a further understanding of the nature and advantages of the invention, reference should be made to the following description taken in conjunction with the accompanying drawings.

DETAILED DESCRIPTION OF THE INVENTION

Figure 1:
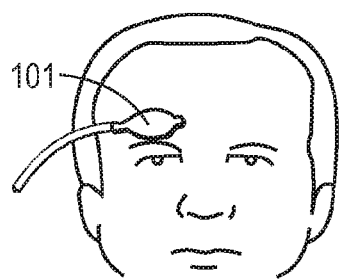
FIG. 1 is a diagram of a forehead oximetry sensor being applied to a patient.

The embodiments of the present invention are directed towards a headband with a tension indicator. Such a headband may be used to support the administration of a health care related service to a patient. Such a service may include the placement of a sensor 101 on a patient's forehead, such as for example, an oximetry sensor (e.g., those manufactured by Nellcor Puritan Bennett, the assignee herein), as is shown in FIG. 1. A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990, and the relationship between oxygen saturation and modulation ratio is further described in U.S. Pat. No. 5,645,059, entitled "MEDICAL SENSOR WITH MODULATED ENCODING SCHEME," issued Jul. 8, 1997, the disclosures of which are herein incorporated by reference in their entirety. Most pulse oximeters extract the plethysmographic signal having first determined saturation or pulse rate. An exemplary forehead oximetry sensor is described in a co-pending U.S. patent application Ser. No. 10/256,245, entitled: "Stacked Adhesive Optical Sensor," the disclosure of which is herein incorporated by reference in its entirety for all purposes.

Figure 2:
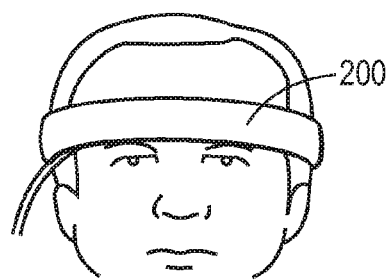
FIG. 2 is a diagram of a forehead oximetry sensor being held to a patient's forehead with a headband.

The force applied to the oximetry sensor can be a factor in the proper functioning of the sensor. In certain clinical scenarios, a headband 200 is required to be used in conjunction with a forehead sensor 101 (e.g., an oximetry sensor), as is shown in FIG. 2. FIG. 2 shows the sensor leads extending from the sensor (not shown) outward from beneath the headband. Such clinical scenarios include scenarios where: patient is lying down with his/her head near or below chest level; patient is subject to elevated venous pressure; patient is diaphoretic; patient is moving excessively, such as during exercise; as well as other scenarios where venous pulsations can introduce errors in oximetry calculations. In those scenarios, without a headband, or force on the oximetry sensor, venous pulsations could cause an incorrect interpretation of the waveform, and therefore result in a less than accurate determination of the oxygen saturation and pulse rate values. The headband can be used to apply pressure to the oximetry sensor, thus reducing the effects of venous pulsations. When used to support an oximetry sensor, the amount of force applied by the sensor on the forehead should be greater than the venous pressure, but less than the arteriole pressure. Generally, a good pressure range is one where the applied pressure is higher than venous pressure (e.g., 3-5 mm Hg) and lower than the capillary pressure (e.g., 22 mm Hg). Preferably, this is between 10 mm Hg and 20 mm Hg in the adult patient. The headband in accordance with the embodiments of the present invention may be adjusted for use with any size wearer by using an adjustable closure mechanism, such as for example a hook and loop closure mechanism. Alternately, the headband may be provided in varying sizes, depending on the general size of the wearer's head; for example using a small headband for a neonate, a larger one for a child and an even larger one for an adult wearer. The user can apply a wide range of pressures to the forehead oximetry sensor depending on the amount of tension which has been applied to the headband during its placement around the wearer's head.

The embodiments of the present invention are intended to alleviate the guesswork by the caregivers by giving them a visual indicator of the proper amount of tension required in the headband during placement around the head. The required tension is related to the pressure being applied by the sensor when it is attached with the patient.

Figure 3:
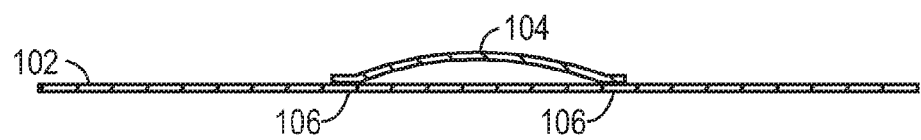
FIG. 3 is a diagram of one embodiment of the headband in accordance with the present invention.
Figure 5:
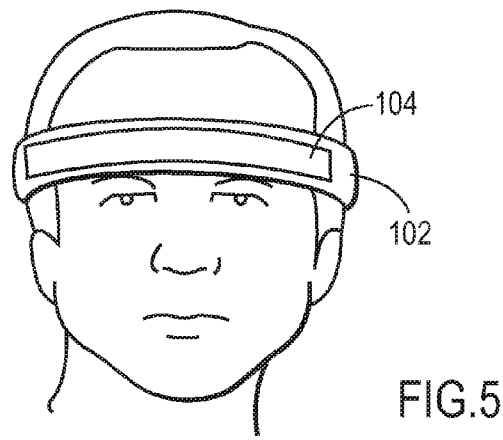
FIG. 5 is a front view diagram of an embodiment of the headband in accordance with the present invention shown worn by a user.
Figure 6:
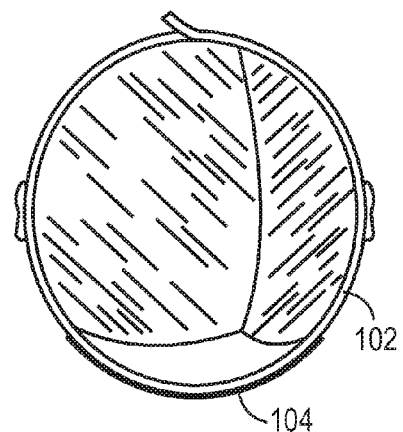
FIG. 6 is a top view diagram of an embodiment of the headband in accordance with the present invention shown in proper tension when worn by a user.
Figure 7:
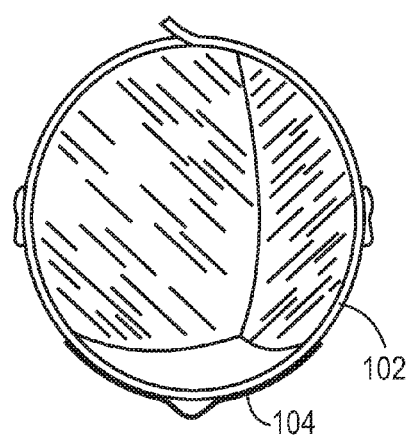
FIG. 7 is a top view diagram of an embodiment of the headband in accordance with the present invention shown in less than proper tension when worn by a user.

In one embodiment, shown in FIG. 3, an elastic headband 102 is shown in an unstretched position. A non-elastic fabric 104 is shown attached to the elastics portion 102 along two of its edges 106. The other two edges of the non-elastic portion are not attached to the elastic segment and are thus free to project outward away from the face of the elastic segment. The non-elastic segment is smaller the elastic segment. The non-elastic segment is sized to span a portion of the elastic segment when the elastic segment is stretched. The non-elastic segment is larger than the portion of the elastic segment it spans when the elastic segment is not stretched. As the elastic segment 102 is stretched from its non-stretched position, the non-elastic portion is pulled at its edges 106 along with the stretching elastic segment 102 until the elastic portion between the edges has stretched to a length equal to the length of the non-elastic portion. The headband also includes closure mechanisms (not shown), which are described below in conjunction with FIG. 4. FIG. 5 shows a front view diagram of an embodiment of the headband in accordance with the present invention shown worn by a user. It is noted that the headband may be used to hold and impart a pressure against a sensor, such as an oximetry sensor applied to a patient's forehead, as shown in FIG. 2. For clarity in describing the tension indicator, such a sensor is not shown in FIGS. 5-7. FIG. 6 is a top view diagram of an embodiment of the headband 102 in accordance with the present invention shown in proper tension when worn by a user. As is shown in this figure, when the headband is properly tightened, the pressure indicator portion 104 is pulled tight across the elastic portion 102, thus not providing a visual indication that the headband needs to be retightened. On the other hand, FIG. 7 shows a top view diagram of an embodiment of the headband in accordance with the present invention shown in less than proper tension when worn by a user. As is shown in FIG. 7, when a less than adequate pressure is being applied by the headband to a user's forehead, or when the headband is not tight enough, the indicator 104 projects out from the surface creating a loop which provides a visual cue that the headband needs retightening.

When the headband is not stretched there is an amount of slack between the non-elastic and elastic portions. When the headband is stretched, the slack in the non-elastic strap is eliminated, giving the visual indication that the headband stretch is sufficient. The headband is chosen to be long enough to fit around the head of a user (or patient). The elastic material may be made of any suitable fabric, such as an open cell urethane foam. The non-elastic strap, which is shorter than the elastic portion is sewn or attached otherwise (e.g., adhesively, etc.) onto the elastic headband at a spacing that is less than the lengths of the non-elastic portion. The non-elastic material may be made of any suitable fabric, such a Dacron-type fabric.

Figure 4A:
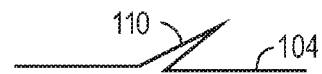
FIG. 4A is a top view detail diagram of the crease or fold of FIG. 4.
Figure 4:
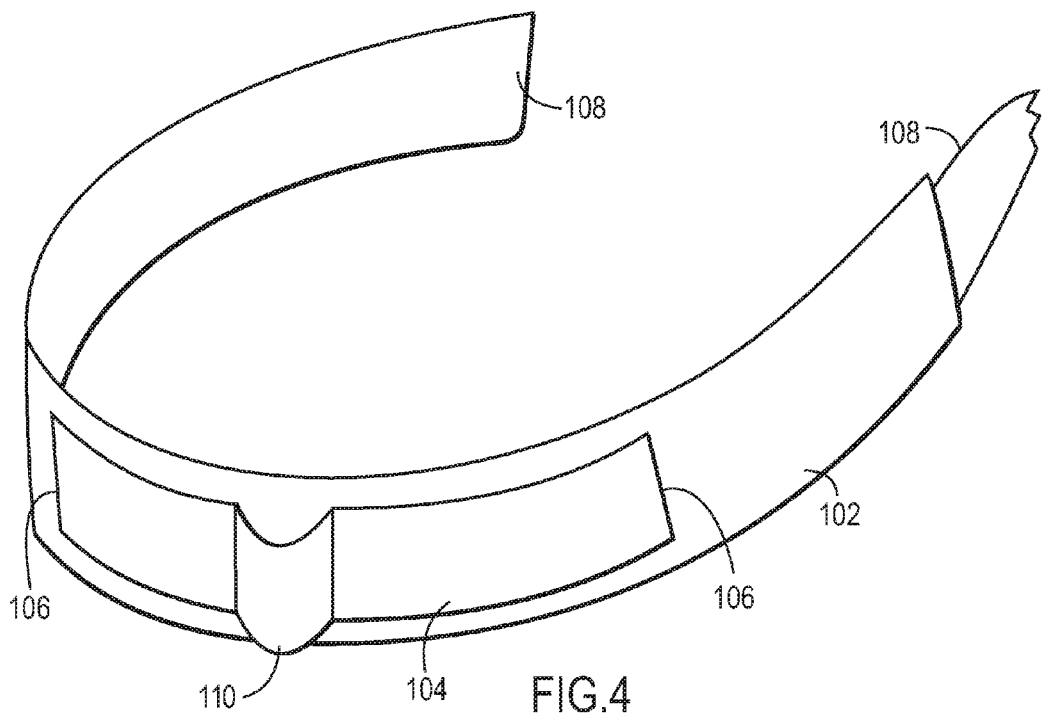
FIG. 4 is a diagram of an alternate embodiment of the headband in accordance with the present invention.

FIG. 4 is a diagram of an alternate embodiment of the headband in accordance with the present invention. An elastic headband 102 is shown in an unstretched position. A non-elastic fabric 104 is shown attached to the elastics portion 102 along two of its edges 106. The other two edges of the non-elastic portion are not attached to the elastic segment and are thus free to project outward away from the face of the elastic segment. The non-elastic segment 104 is smaller the elastic segment 102. The non-elastic segment is sized to span a portion of the elastic segment when the elastic segment is stretched. The non-elastic segment is larger than the portion of the elastic segment it spans when the elastic segment is not stretched. As the elastic segment 102 is stretched from its non-stretched position, the non-elastic portion is pulled at its edges 106 along with the stretching elastic segment 102 until the elastic portion between the edges has stretched to a length equal to the length of the non-elastic portion.

FIG. 4 also shows the non-elastic portion to include a permanent crease or a fold 110. As shown in FIG. 4A, such a fold 110 may be made by overlapping the non-elastic portion to form a fold and then heat pressing or heat sealing the fabric to form a permanent fold or crease. In one embodiment, the fold or crease is made in the middle of the inelastic segment, which causes it to project outward in a sharp, angular fashion as the elastic band 102 retracts or relaxes. In operation, it has been shown that the sharp, angular crease or fold acts as a mechanical amplifier and provides a more distinct visual cue and better sensitivity as to when the threshold of minimal headband tension has been passed. The creased tension indicator 110 exhibits increased sensitivity to a loss in headband tension by projecting further away from the elastic band in a skewed fashion. The creased tension indicator 110 provides a more pronounced visual cue both from the perspective of looking directly at the forehead and from looking down at the top (edge) of the headband. The material chosen for the inelastic portion having a fold or a crease can be similar to the noncreased or nonfolded inelastic material. In addition, a material such a polyester webbing material, which is capable of holding a fold or a crease, may also be used. The elastic material may be made of a material as is described above, or made using other suitable material such as a terry band.

When the headband is not stretched there is an amount of slack between the non-elastic and elastic portions. When the headband is stretched, the slack in the non-elastic strap is eliminated, giving the visual indication that the headband stretch is sufficient.

Also shown in FIG. 4, and applicable to the embodiment described in conjunction with FIG. 3, is the closure device 108. One such closure device is a hook and loop type closure. The headband in accordance with the embodiments of the present invention may use other closure mechanisms such as snaps, buttons, adhesives, pins, or combinations thereof, as well as others known to those of skill in the relevant arts. Alternately, the headband may be a pre-formed loop, without a separate closure mechanism.

The headband described above includes a sensor attachment pressure indicator. As described above, the headband may be used to allow a sensor's attachment pressure with the patient's tissue location (e.g. forehead, and so on) to be chosen which is greater than venous pulsations (e.g., 5-10 mm Hg) but less than a maximum amount (e.g., 30 mm Hg, or so). As described above, such a pressure indicator is attached with the headband. Alternately, the pressure indicator may be attached with the sensor, such as an oximetry sensor. One embodiment of the pressure indicator is a tension indicator as described above with reference to FIGS. 3-4. Other pressure indicating means include pressure or force sensors small and light enough to be included with either the sensor or the headband assembly.

The information provided by the pressure indicator may be used to help establish an acceptable windows of pressure for the sensor's attachment with a patient. The acceptable window of pressure may also be enhanced to include the affects of the patient's head elevation relative to the patient's heart.

Additionally, the concept of using a headband to ensure an acceptable sensor attachment pressure is extendible to other patient body locations; locations where a sensor attachment pressure can help provide a more accurate sensor reading.

Figure 8:
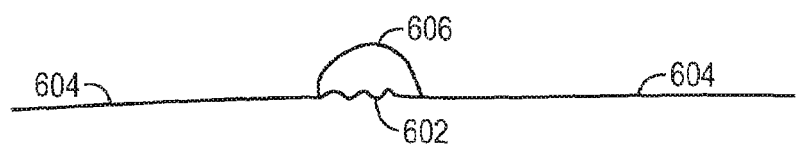
FIG. 8 is a diagram of an alternate embodiment of the headband in accordance with the present invention.

An alternate embodiment of the tension or pressure indicating headband in accordance with the present invention is shown in FIG. 8. As is shown in FIG. 8, the headband includes an inelastic portion 604 and an elastic portion 602. The tension indicating portion 606 is also made of an inelastic material. The tension indicating portion 606 may be a creased or folded as described in conjunction with FIG. 4 or as is shown uncreased or unfolded as described in conjunction with FIG. 3. The description of the closure devices and how the elastic and inelastic portions are attached to one another are also set forth above. In this embodiment, the main stretchable portion is elastic portion 602. Once the headband has been stretched such that section 602 is stretched to match the length of section 606, the headband's stretch will be limited. This embodiment by having a shorter elastic portion limits the extension of the headband and hence limits the range of pressures that can be applied by the headband against a user's forehead or the sensor applied to a user's forehead.

Figure 9:
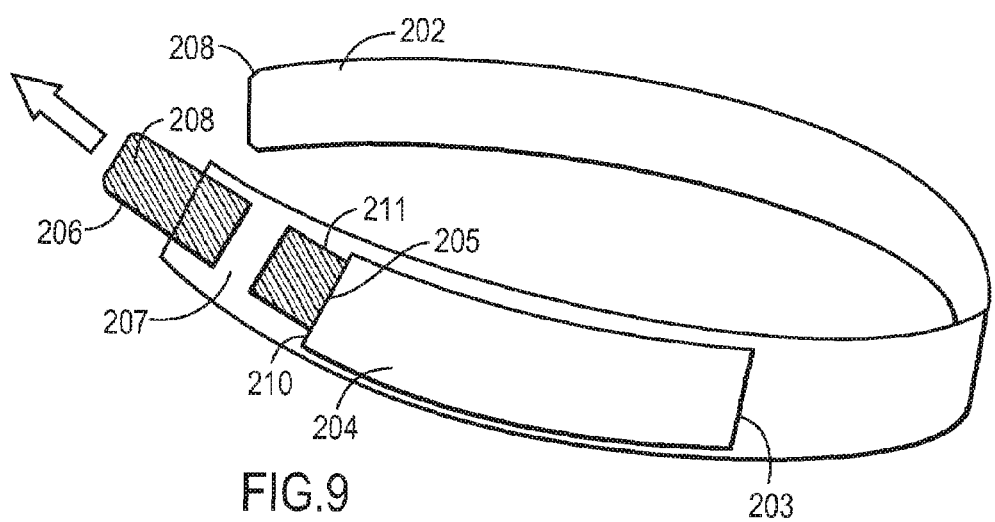
FIG. 9 is a diagram of an alternate embodiment of the headband in accordance with the present invention.

FIG. 9 is an exemplary diagram of an alternate embodiment of the headband in accordance with the present invention. The headband may be used for the purpose of applying a small, controlled amount of pressure against the forehead of its wearer. As set forth above, when used to support an oximetry sensor, the amount of force applied by the sensor on the forehead should be greater than the venous pressure, but less than the arteriole pressure. Generally, a good pressure range is one where the applied pressure is higher than venous pressure (e.g., 3-5 mm Hg) and lower than the capillary pressure (e.g., 22 mm Hg). Preferably, this is between 10 mm Hg and 20 mm Hg in the adult patient. The headband in accordance with the embodiments of the present invention may be adjusted for use with any size wearer by using an adjustable closure mechanism, such as for example a hook and loop closure mechanism. Alternately, the headband may be provided in varying sizes, depending on the general size of the wearer's head; for example using a small headband for a neonate, a larger one for a child and an even larger one for an adult wearer. The user can apply a wide range of pressures to the forehead oximetry sensor depending on the amount of tension which has been applied to the headband during its placement around the wearer's head. In one embodiment, the different head sizes of the wearer's are accommodated by providing a suite of different sized headbands; starting with the smallest and graduating to larger sized ones; all having common features as described herein. In another embodiment, a hook and loop type closure device is configured such that the entire back side of the low stretch band (described below) is capable of engaging an end of the headband having the mating hook and loop surface. In this manner, a one size headband is enabled to accommodate any size head. Further details are described below.

The embodiment shown in FIG. 9 enables a clinician to accurately and consistently apply the headband with the proper tension in an intuitive manner as described below. As shown in FIG. 9, the headband includes a substantially inelastic, or low stretch band 202 having a closure device 208 on or near its end and preferably on a portion of or the entire outer surface thereof. One such closure device is a hook and loop type closure. The headband in accordance with the embodiments of the present invention may use other closure mechanisms such as snaps, buttons, adhesives, pins, or combinations thereof, as well as others known to those of skill in the relevant arts. The inelastic or low stretch band 202 can be made of any type of low-stretch fabric, such as a Nylon, polyester or equivalent materials, including those described above.

The headband also includes an elastic segment 204 of a specific length, to provide a specific spring force once stretched, attached at one end 203 to the outer facing side of the low stretch material (i.e. band 202) that wraps around the patient's head. The attachment of the elastic segment 204 to band 202 at 203 may be achieved by sewing the segment 204 at 203 to 202. Alternately, the segment 204 may be adhesively attached to band 202 at 203. At the other, free end, 205 the elastic segment 204 is configured to be attached with a segment of band 202 using a closure device 208, as described above (e.g., inelastic material that has a patch of Velcro™ hook material). In one embodiment, the free end 205 of the elastic segment is attached with a low stretch portion or tab 206, which attaches with a segment of band 202 using a closure device 208 to form a closable loop. The band 206 slips through slots in the band 202 at the stop 207, in a manner similar to a belt through a loop. To apply a proper tension, and hence a proper amount of pressure against the skin, to the low stretch material band 202 wrapped around the head, the elastic segment 204 is stretched a controlled distance, and then fastened to the low stretch strip 202 using the closure device 208. The stretch of the elastic segment 204 is controlled, as it meets a physical stop. In one embodiment, the physical stop is provided by having the width of the elastic portion 204 sized slightly larger than the opening of the stop 207 in the band 202, and thus once stretched a certain distance, the elastic portion 204 meets a physical stop 207. The stop 207 may be an opening in the band 202 that is slightly smaller in width than the elastic portion 204. Alternately, the stop may be provided by a narrow band similar in shape and function to a belt loop that is sewn on or attached with the band 202. By stretching and fastening the elastic portion 204 with the band 202, the tension in the elastic segment 204 is transferred to the entire low stretch strip that is wrapped around the patient's head. This controlled tension, in turn, translates into a controllable pressure against the patient's forehead skin. In other words, proper tension in the band and hence proper pressure against the forehead of the patient is achieved by wrapping the band 202 around a patient's head; then pulling on the elastic segment directly or via a pulling force on the member 206 to extend the elastic segment 204 until its edge 210 meets the stop 207, and then securing the free end of segment 206 against the band 202 using the closure device 208.

The headband also includes a visual indicator that is used to monitor the stretch of the elastic portion 204. In one embodiment, the tab 206 includes a visible or indicator portion 211 between the free end of the elastic portion 205 and the stop 207, such that when the headband is properly tensioned, the elastic portion 204 is stretched and thus portion 211 is no longer visible, as the elastic portion 204 abuts against the stop 207. Alternately, headband includes visual indicator 212 (shown in FIG. 10D' and 10D"), that enable the visual monitoring of the edge of the free end of the elastic segment 204 against the indicator 212, as the segment 204 is stretched. While the indicator 212 is shown as a notch, it can be a line, or any other suitable marker. The headband described herein provides structures that monitor and/or control the stretch of the elastic segment 204. The stretch of the elastic segment is controlled by the stop 207. The stop 207 ensures that the elastic segment's stretch is limited, as describe above. For example, a clinician is prevented from over stretching the elastic segment, since the free edge of the elastic segment will meet against the stop 207 once it is fully stretched. The visual indicator 211 or 212 enable the monitoring of the amount of the stretch of the elastic segment. In addition, the adequacy of the tension or stretch of the segment is monitored visually by observing either the indicator 211 or the position of the free edge of the segment against the indicator 212. So, for example, once the headband has been properly applied, it is expected that the headband or portions thereof may relax and in which case the visual indicators will show that the headband needs re-tensioning.

Figure 10A:
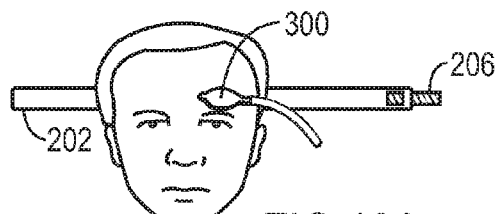
FIG. 10A-E are diagrams showing the method of placing the headband of FIG. 9 on a patient's head.
Figure 10E:
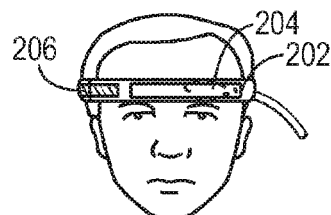
Figure 10B:
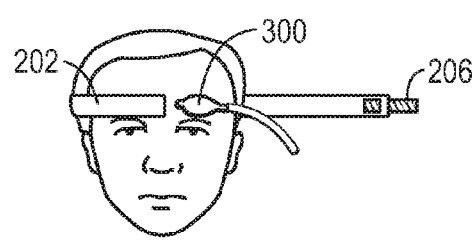
Figure 10C:
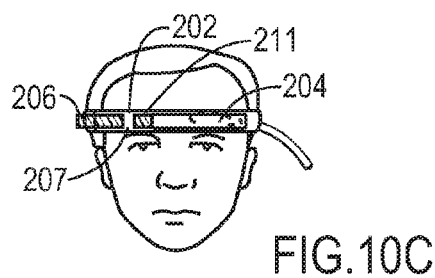
Figure 10D:
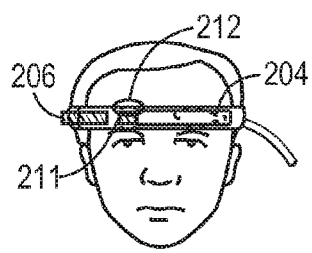
Figure 10D:
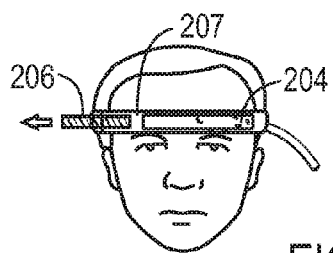
Figure 10D:
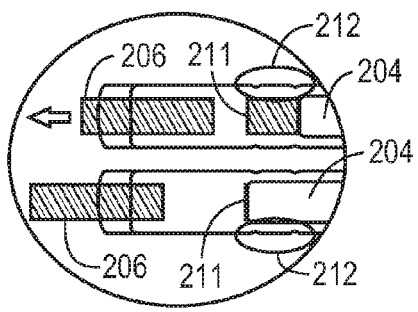

FIGS. 10A-E are diagrams showing the method of placing the headband of FIG. 9 on a patient's head. For ease of description, it is assumed that the patient or headband wearer is lying down on his (or her) back on a surface and facing up. As shown in FIG. 10A, first the headband is placed under the patient's head with the elastic segment side facing down and on the same side as that of a forehead oximetry sensor 300. For ease of placement, it is preferred to allow the length of the band to extend more on the elastic segment side. Next, as shown in FIG. 10B, the shorter end is rolled towards the patient's forehead. Next, as shown in FIG. 10C, the elastic segment side is rolled over the patient's forehead covering the sensor 300. It may be preferable to provide a sensor design outline on the elastic portion of the headband, in which case it is preferred to align the sensor outline on the elastic band portion of the forehead sensor approximately with the sensor 300. Next, as shown in FIG. 10D, the tab 206 is pulled until the elastic portion 204 reaches the stop 207 and indicator or visible portion 211 of the band is no longer visible. Note that the tab 206 has a portion 211 (e.g., indicator portion) that is partially visible between the elastic portion 204 and the stop 207 in FIG. 10C, when the band in not adequately stretched, and the same tab portion 211 (e.g., indicator portion) is no longer visible between the elastic portion 204 and stop 207 when the elastic portion is adequately stretched, as shown in FIGS. 10D and 10E. Alternately, as shown in FIGS. 10D'-D", after the elastic segment side is rolled over the patient's forehead covering the sensor 300, the tab 206 is pulled until the elastic segment 204 reaches the position mark or indicator 212. An adequately stretched headband is enabled to impart an adequate tension in the headband and hence an adequate pressure against the forehead and the sensor that is placed between the forehead and the headband. Therefore, when there is no tab portion 211 visible between the elastic portion 204 and the stop 207, or when the elastic segment is properly aligned with the indicator 212, or when the elastic portion has been adequately stretched against its stop, the clinician has an indicator that a proper pressure is being applied to the wearer's forehead.

Figure 11:
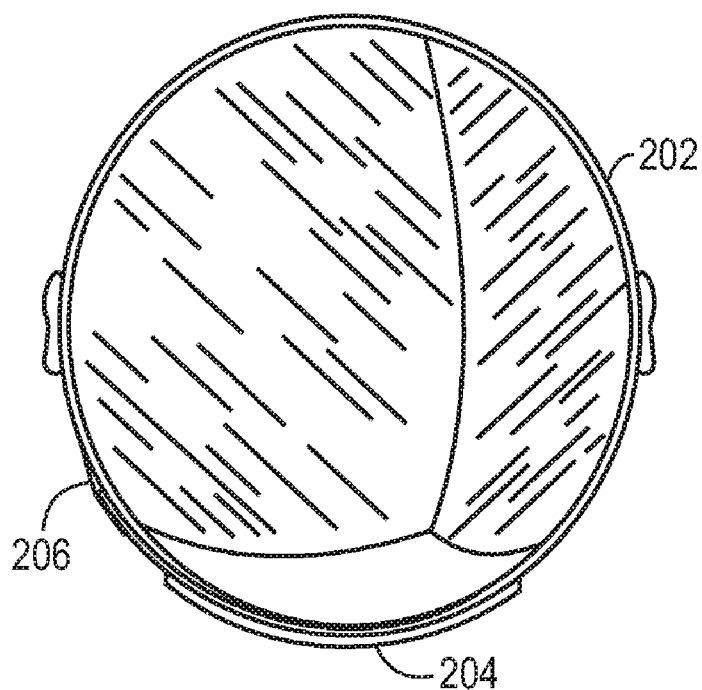
FIG. 11 is a top view diagram of the headband of FIG. 9 when placed on a patient's head.

FIG. 11 is a top view diagram of the headband of FIG. 9 when placed on a patient's head with an adequate tension. As can be seen, band 202 is wrapped around the patient's head, elastic portion 204 is adequately stretched and fastened with the band 202 via tab portion 206.

As will be understood by those skilled in the art, the present invention may be embodied in other specific forms without departing from the essential characteristics thereof. These other embodiments are intended to be included within the scope of the present invention, which is set forth in the following claims.

What is claimed is:

1. A headband for applying pressure to an oximetry sensor on the forehead of a patient, comprising:
   a low stretch segment sized to fit around a patient's head;
   an elastic segment being smaller than the low stretch segment, the elastic segment having a free end and an attached end, the elastic segment being attached at the attached end with the low stretch segment;

a tab portion having a first end and a second end, the first end of the tab portion being connected to the free end of the elastic portion, the second end of the tab portion configured to form a closed loop with the low stretch segment around a patient's head;

a visual indicator configured for monitoring the extended position of the free end of the elastic segment;

a stop portion configured to engage against the elastic segment to limit the stretch of the elastic segment, the stop portion comprising an opening having a width that is smaller than the width of the low stretch segment and the width of the elastic segment; and a closure mechanism configured to couple the second end of the tab portion with the low stretch segment to secure the closed loop.

2. The headband of claim 1 wherein the visual indicator is on the tab portion between its first end and the stop portion such that the indicator portion when visible indicates that the headband needs re-tightening; and when the indicator portion is not visible it indicates an adequate level of tension corresponding with delivering a pressure in the range higher than the venous pressure and lower than the capillary pressure to the forehead of the patient.

3. The headband of claim 1 wherein the visual indicator comprises a notch, a line, a marking, or a combination thereof on the low stretch segment.

4. The headband of claim 1 wherein the closure mechanism is a hook and loop closure, a snap, a button, an adhesive, or a pin, or a combination thereof.

5. A headband, comprising:

a low stretch segment sized to fit around a wearer's head;

an elastic segment being smaller than the low stretch segment, the elastic segment having a free end and an attached end, the elastic segment being attached at the attached end with the low stretch segment:

a tab portion having a first end and a second end, the first end of the tab portion being connected with the free end of the elastic portion, the second end of the tab portion configured to form a closed loop with the low stretch segment: and a stop portion configured to engage against the elastic segment to limit the stretch of the elastic segment, wherein the tab portion comprises an indicator portion between the free end of the elastic portion and the stop portion, such that the indicator portion, when visible, indicates that the headband needs re-tightening; and when the indicator portion is not visible it indicates an adequate level of tension corresponding with delivering a pressure in a range higher than venous pressure and lower than capillary pressure to the wearer's head.

6. A headband, comprising:

a low stretch segment sized to fit around a wearer's head;

an elastic segment being smaller than the low stretch segment, the elastic segment having a free end and an attached end, the elastic segment being attached at the attached end with the low stretch segment;

a tab portion having a first end and a second end, the first end of the tab portion being connected with the free end of the elastic portion, the second end of the tab portion configured to form a closed loop with the low stretch segment;

an indicator configured to indicate whether the headband is applying pressure in a given range when the headband is around the wearer's head, wherein the indicator comprises a marker associated with the free end of the elastic segment, such that pulling the tab outwardly along the headband moves the free end of the elastic segment relative to the marker to indicate whether the headband is delivering a level of tension corresponding to a pressure in a range higher than venous pressure and lower than capillary pressure to the wearer's head.

7. A headband, comprising:

a low stretch segment sized to fit around a wearer's head;

an elastic segment being smaller than the low stretch segment, the elastic segment having a free end and an attached end, the elastic segment being attached at the attached end with the low stretch segment, the free end of the elastic segment configured to form a closed loop with the low stretch segment around a wearer's head; and a sensor configured to be placed on a wearer's head and to be forced against the wearer's head via pressure from the headband.

8. The headband of claim 7, comprising a pressure sensor coupled to the sensor or to the headband.

9. The headband of claim 8, wherein the pressure sensor is visible from a side of the headband not in contact with the wearer's head.

10. The headband of claim 1, comprising a sensor configured to be placed on the patient's head and to be forced against the patient's head via pressure from the headband.

11. The headband of claim 10, comprising a pressure sensor coupled to the sensor or to the headband.

12. The headband of claim 11, wherein the pressure sensor is visible from a side of the headband not in contact with the patient's head.

13. A headband at least long enough to encircle a wearer's head, comprising:

a substantially inelastic band having a first end portion and a second end portion;

an elastic band having a first end and a second end, wherein the first end of the elastic band is attached to the substantially inelastic band;

a tab having a first end and a second end, wherein the first end of the tab is attached to the second end of the elastic band, and the second end of the tab is configured to extend outwardly from the second end portion of the substantially inelastic band and to couple to the first end portion of the substantially inelastic band;

a visual indicator configured to indicate a position of the second end of the elastic band;

a sensor configured to be placed on the wearer's head and to be forced against the wearer's head via pressure from the headband; and a pressure sensor coupled to the sensor or to the headband.

14. The headband of claim 13, wherein the pressure sensor is visible from a side of the headband not in contact with the wearer's head.

15. A headband at least long enough to encircle a wearer's head, comprising:

a substantially inelastic band having a first end portion and a second end portion;

an elastic band having a first end and a second end, wherein the first end of the elastic band is attached to the substantially inelastic band;

a tab having a first end and a second end, wherein the first end of the tab is attached to the second end of the elastic band, and the second end of the tab is configured to extend outwardly from the second end portion of the substantially inelastic band and to couple to the first end portion of the substantially inelastic band;

a visual indicator configured to indicate a position of the second end of the elastic band; and a stop configured to limit stretching of the elastic band, wherein the stop comprises an opening in the substantially inelastic band having a width large enough for the tab to pass through, but small enough to restrain the elastic band from passing through.

16. A headband at least long enough to encircle a wearer's head, comprising:

a substantially inelastic band;

an elastic band having one end attached to the substantially inelastic band, and configured to be pulled in a direction away from the end attached to the substantially inelastic band and in a direction along the headband when the headband is around the wearer's head, and configured to stretch when pulled such that the tension created when stretched applies pressure to the wearer's head;

a visual indicator configured to indicate whether the pressure applied to the wearer's head from the headband is in a pressure range higher than venous pressure and lower than capillary pressure; and a sensor configured to be placed on the wearer's head and to be forced against the wearer's head via pressure from the headband.

17. The headband of claim 16, comprising a pressure sensor coupled to the sensor or to the headband.

18. The headband of claim 17, wherein the pressure sensor is visible from a side of the headband not in contact with the wearer's head.

* * * * *